(12) United States Patent
Forsberg et al.

(10) Patent No.: US 7,598,061 B2
(45) Date of Patent: Oct. 6, 2009

(54) MOLD INFECTIONS

(75) Inventors: Neil E. Forsberg, Corvallis, OR (US); Steven B. Puntenney, Independence, OR (US)

(73) Assignee: The State of Oregon, Acting By and Through the State Board of Higher Education; Oregon State Univ, Corvallis, OR (US)

( * ) Notice: Subject to any disclaimer, the term of this patent is extended or adjusted under 35 U.S.C. 154(b) by 103 days.

(21) Appl. No.: 11/724,596

(22) Filed: Mar. 14, 2007

(65) Prior Publication Data

US 2007/0238120 A1    Oct. 11, 2007

Related U.S. Application Data

(62) Division of application No. 10/776,646, filed on Feb. 10, 2004, now abandoned.

(60) Provisional application No. 60/446,367, filed on Feb. 10, 2003.

(51) Int. Cl.
*C12Q 1/68* (2006.01)
*C12P 19/34* (2006.01)

(52) U.S. Cl. ..................... 435/91.2; 435/6; 435/91.1

(58) Field of Classification Search .................. None
See application file for complete search history.

(56) References Cited

U.S. PATENT DOCUMENTS 6,872,523 B1 * 3/2005 Iwen et al. ................. 435/6

OTHER PUBLICATIONS

Costa et al., "Development of two real-time quantitative TaqMan PCR assays to detect circulating *Aspergillus fumigatus* DNA in serum," Journal of Microbiological Methods, 2001, vol. 44, pp. 263-269.*
Buck et al., "Design Strategies and Performance of Custom DNA Sequencing Primers," BioTechniques, Sep. 1999, vol. 27, pp. 528-536.*
Abutarbush et al., "Jejunal hemorrhage syndrome in dairy and beef cattle: 11 cases (2001 to 2003)," The Canadian Veterinary Journal, Aug. 2005, vol. 46, No. 8, pp. 711-715.*
Schallibaum et al., "*Aspergillus nidulans* and *Aspergillus fumigatus* as causal agents of bovine mastitis," Medical Mycology, 1980, vol. 18, issue 1, Abstract only, print out pp. 1-2, [retrieved on-line from http://informaworld.com/smpp/content~content=a782301689~db=all, retrieval date Oct. 29, 2008.*

* cited by examiner

*Primary Examiner*—Young J Kim
(74) *Attorney, Agent, or Firm*—Dann, Dorfman, Herrell & Skillman; Robert C. Netter, J.D.

(57) ABSTRACT

Methods are disclosed for detecting, quantifying and/or identifying a fungal species in a sample or for diagnosing jejunal hemorrhage syndrome in a subject. The methods generally include amplifying a fungal nucleic acid sequence present in the sample using a primer selected from the group consisting of: SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16; and observing or measuring the amplified nucleic acid sequence. The fungal species can thereby be detected, quantified, and/or identified. Fungal contamination also can be detected or measured in a biological or feed or food sample.

14 Claims, 3 Drawing Sheets

```
                         SEQUENCE LISTING

<160> NUMBER OF SEQ ID NOS: 16

<210> SEQ ID NO 1
<211> LENGTH: 29
<212> TYPE: DNA
<213> ORGANISM: Artificial Sequence
<220> FEATURE:
<223> OTHER INFORMATION: Synthetic  Construct

<400> SEQUENCE: 1
agggatgtat ttattagata aaaaatcaa                                            29

<210> SEQ ID NO 2
<211> LENGTH: 25
<212> TYPE: DNA
<213> ORGANISM: Artificial Sequence
<220> FEATURE:
<223> OTHER INFORMATION: Synthetic  Construct

<400> SEQUENCE: 2
cgcagtagtt agtcttcagt aaatc                                                25

<210> SEQ ID NO 3
<211> LENGTH: 21
<212> TYPE: DNA
<213> ORGANISM: Artificial Sequence
<220> FEATURE:
<223> OTHER INFORMATION: Synthetic  Construct

<400> SEQUENCE: 3
ccaatgccct tcggggctcc t                                                    21

<210> SEQ ID NO 4
<211> LENGTH: 17
<212> TYPE: DNA
<213> ORGANISM: Artificial Sequence
<220> FEATURE:
```

```
<223> OTHER INFORMATION: Synthetic Construct

<400> SEQUENCE: 4
cctggttccc cccacag                                                    17

<210> SEQ ID NO 5
<211> LENGTH: 19
<212> TYPE: DNA
<213> ORGANISM: Artificial Sequence
<220> FEATURE:
<223> OTHER INFORMATION: Synthetic Construct

<400> SEQUENCE: 5
gaagaacgca gcgaaatgc                                                  19

<210> SEQ ID NO 6
<211> LENGTH: 19
<212> TYPE: DNA
<213> ORGANISM: Artificial Sequence
<220> FEATURE:
<223> OTHER INFORMATION: Synthetic Construct

<400> SEQUENCE: 6
ccaacacaca agccgtgct                                                  19

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
ggtgaggcct tcggactg                                                   18

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
cctccgctta ttgatatgct taag                                            24

<210> SEQ ID NO 9
<211> LENGTH: 22
<212> TYPE: DNA
<213> ORGANISM: Artificial Sequence
<220> FEATURE:
<223> OTHER INFORMATION: Synthetic Construct

<400> SEQUENCE: 9
cgtaacaagg tttccgtagg tg                                              22

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gcgggtatcc ctacctgatc                                                 20
```

```
<210> SEQ ID NO 11
<211> LENGTH: 21
<212> TYPE: DNA
<213> ORGANISM: Artificial Sequence
<220> FEATURE:
<223> OTHER INFORMATION: Synthetic  Construct

<400> SEQUENCE: 11
aacctcccac ccgtgtctat c                                              21

<210> SEQ ID NO 12
<211> LENGTH: 15
<212> TYPE: DNA
<213> ORGANISM: Artificial Sequence
<220> FEATURE:
<223> OTHER INFORMATION: Synthetic  Construct

<400> SEQUENCE: 12
gcggccgtcg aaacg                                                     15

<210> SEQ ID NO 13
<211> LENGTH: 18
<212> TYPE: DNA
<213> ORGANISM: Artificial Sequence
<220> FEATURE:
<223> OTHER INFORMATION: Synthetic  Construct

<400> SEQUENCE: 13
gccggagaca ccacgaac                                                  18

<210> SEQ ID NO 14
<211> LENGTH: 28
<212> TYPE: DNA
<213> ORGANISM: Artificial Sequence
<220> FEATURE:
<223> OTHER INFORMATION: Synthetic  Construct

<400> SEQUENCE: 14
cgatacaatc aactcagact tcactaga                                       28

<210> SEQ ID NO 15
<211> LENGTH: 17
<212> TYPE: DNA
<213> ORGANISM: Artificial Sequence
<220> FEATURE:
<223> OTHER INFORMATION: Synthetic  Construct

<400> SEQUENCE: 15
ccgagtgcgg gtcctttt                                                  17

<210> SEQ ID NO 16
<211> LENGTH: 23
<212> TYPE: DNA
<213> ORGANISM: Artificial Sequence
<220> FEATURE:
<223> OTHER INFORMATION: Synthetic  Construct

<400> SEQUENCE: 16
ccgaagcaac agggtacaat aga                                            23
```

MOLD INFECTIONS

CROSS REFERENCE TO RELATED APPLICATIONS

This application is a divisional of U.S. application Ser. No. 10/776,646, filed on Feb. 10, 2004 now abandoned, which claims priority from U.S. application Ser. No. 60/446,367, filed on Feb. 10, 2003, both of which are incorporated herein by reference for all purposes.

BACKGROUND OF THE INVENTION

The present disclosure relates to methods of detecting, quantifying, and identifying a fungal species in a sample, particularly for the detection or diagnosis of jejunal hemorrhage syndrome.

Jejunal hemorrhage syndrome (JHS), also known as hemorrhagic bowel syndrome (HBS) and dead gut syndrome, is a newly-described disorder primarily affecting dairy cattle. Symptoms of JHS include point-source sub-mucosal hematomas, and can include ruptured hematomas with exsanguination into the lumen of the jejunum. The hematomas originate in the jejunal submucosa, and they dissect the mucosa from the underlying connective tissue. Despite the hemorrhage, clotting is unaffected.

JHS is characterized by a sudden drop in milk production, abdominal pain due to obstructed bowel, and anemia. Death generally comes within 48 hours from the onset of the obstructing blood clot plug. Fatal factors are presumed to be anemia, combined with digesta stagnation in much of the severely dilated small intestine proximal to the plug. First described in 1991, JHS incidence is increasing (see, e.g., Cantor, "Jejunal hemorrhage syndrome: a new emerging disease of dairy cows?"*Washington State Vet. Med. Assoc. Newslett.*, July, 1999; St. Jean and Anderson, "Intraluminal-intramural hemorrhage of the small intestine in cattle," Current *Veterinary Therapy Food Animal Practice* 4th Ed, Howard and Smith eds., Philadelphia. W. B. Saunders. 539:1999) and is responsible for at least 2% of the deaths of dairy animals in the United States (Baker, "Be on the lookout for hemorrhagic bowel syndrome," *Hoard's Dairyman,* 776, November, 2002).

The cause of JHS is unknown; many potential causes have been investigated and discarded. Potential etiological agents that have been eliminated include parasites, bovine viral diarrhea, coccidia, *salmonella*, coagulopathies, intestinal foreign bodies, physical obstructions, and deformities including volvulus and intussuception. Furthermore, analyses of diets, ages of cows, levels of milk production and a full spectrum of blood chemistry and biochemical assets have failed to reveal a consistent clinical correlate to JHS.

SEQUENCE LISTING

The nucleic sequences are listed in the accompanying sequence listing and are shown using standard letter abbreviations for nucleotide bases as defined in 37 C. F. R. 1.822. Only one strand of each nucleic acid sequence is shown, but the complementary strength is understood as included by any reference to the displayed strand. In the accompanying sequence listing:

SEQ. ID NO: 1 is the nucleic acid sequence of the F1 primer.

SEQ. ID NO: 2 is the nucleic acid sequence of the R1 primer.

SEQ. ID NO: 3 is the nucleic acid sequence of the F2 primer.

SEQ. ID NO: 4 is the nucleic acid sequence of the R2 primer.

SEQ. ID NO: 5 is the nucleic acid sequence of the F4 primer.

SEQ. ID NO: 6 is the nucleic acid sequence of the R3 primer.

SEQ. ID NO: 7 is the nucleic acid sequence of the F4 primer.

SEQ. ID NO: 8 is the nucleic acid sequence of the R4 primer.

SEQ. ID NO: 9 is the nucleic acid sequence of the F5 primer.

SEQ. ID NO: 10 is the nucleic acid sequence of the R5 primer.

SEQ. ID NO: 11 is the nucleic acid sequence of the Sybr-ITS-F1 primer.

SEQ. ID NO: 12 is the nucleic acid sequence of the Sybr-ITS-R1 primer.

SEQ. ID NO: 13 is the nucleic acid sequence of the *A. flavus* F primer.

SEQ. ID NO: 14 is the nucleic acid sequence of the *A. flavus* R primer.

SEQ. ID NO: 15 is the nucleic acid sequence of the *A. niger* F primer.

SEQ. ID NO: 16 is the nucleic acid sequence of the *A. niger* R primer.

DETAILED DESCRIPTION OF THE PREFERRED EMBODIMENT(S)

Terms

Unless otherwise noted, technical terms are used recording to conventional usage. Definitions of common terms and molecular biology may be found in Benjamin Lewin, *Genes V* (Oxford University Press, 1994); *The Encyclopedia Of Molecular Biology* (Blackwell Science, Ltd., 1994); and *Molecular Biology And Biotechnology: A Comprehensive Desk Reference* (VCH Publications, Inc., 1995).

In order to facilitate review of the various embodiments of this disclosure, the following explanations in specific terms are provided:

Amplification refers to techniques that increase the number of copies of a nucleic acid molecule to the sample or specimen. An example of an in vitro amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify copies of the nucleic acid.

Other examples of in vitro amplification techniques include strand displacement implication; transcription-free isothermal amplification; repair chain reaction amplification;

ligase chain reaction amplification; gap filling ligase chain reaction amplification; coupled ligase detection and PCR; and NASDA RNA transcription-free amplification. The product of the in vitro amplification may be characterized by electrophoresis, restriction endonuclease cleavage patterns, oligonucleotide hybridization or ligation, and/or nucleic acid sequencing, using standard techniques.

Animal: A living multi-cellular vertebrate or in vertebrate organism, a category that includes, for example, mammals and birds. The term "animal" includes both humans and non-human mammals. Similarly, the term "subject" includes both human and veterinary subjects.

Antisense, sense, and antigene: Double-stranded DNA (dsDNA) has two strands: a 5'-to-3' strand, referred to as the plus strand, and a 3'-to-5' strand (the reverse complement), referred to as the minus strand. Because RNA polymerase adds nucleic acids in a 5'-3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or complementary to either RNA or plus strand DNA. Sense molecules are molecules that are specifically hybridizable or specifically complementary to the minus strand of DNA. Antigene molecules are either antisense or sense molecules complementary to a dsDNA target. In one embodiment, an antisense molecule specifically hybridizes to a target mRNA and inhibits translation of the target mRNA.

*Aspergillus*: Any of various fungi of the genus *Aspergillus*, which includes many common fungi. *Aspergillus* is a large fungal genus containing more than one hundred species. Of these, *A. fumigatus* and *A. flavus* are the most pathogenic.

Pathogenicity of *Aspergillus* is attributed to three virulence factors: (1) production of iron-sequestering siderophores; (2) secretion of complement- and phagocytic-inhibitory lipids; and (3) secretion of proteases. Specifically, *A. fumigatus* is able to meet its iron requirement, and thereby maintain growth, by the actions of its proteolytic enzymes. These enzymes liberate the host's Fe stores from transferring and lactoferrin and allow Fe transfer to triacetylfusarimine and ferriciocin. In addition, invasiveness is facilitated by secretion of polar and neutral lipids, phenolic compounds and heterocyclic toxins (including aflatoxins and other toxins). Some of these secretions inhibit phagocytosis, while others suppress the immune response of the host by inhibiting complement factors C3a and C5a. Finally, pathogenic species of *Aspergillus* secrete proteases which facilitate hyphal penetration from a colonization site into the underlying parenchymal tissue.

*A. fumigatus* is ubiquitous in the environment, yet it rarely causes serious disease in healthy individuals. Immunocompetence is the primary predisposing factor in *Aspergillus* infection (invasive aspergillosis) in humans. Patients with AIDS, cancer and those receiving organ transplants are particularly susceptible to invasive aspergillosis. For example, invasive aspergillosis occurs in 2.6-10.3% of all bone marrow transplant patients and has a mortality rate of 56-88.1%.

Biological sample: A sample obtained from a plant or animal subject. As used herein, biological samples include all clinical samples useful for the detection of fungal infection in subjects and feed, including, but not limited to, body fluids, tissues and cells. A body fluid is a natural bodily fluid or secretion such as blood, semen, or saliva. In some embodiments, a body fluid is blood, derivatives and fractions thereof, tears, milk, surface washings, urine, cerebrospinal fluid, pus, sputum, bronchoalveolar lavage fluid, ocular fluid, saliva or fecal fluid. A tissue is an aggregation of morphologically similar cells and associated intercellular matter acting together to perform one or more specific functions in the body. For example, a tissue can include, but is not limited to, muscle, nerve, epidermal, or connective tissue. In some embodiments, a tissue sample is a sample of liver, intestine, mesenteric lymph node, cotyledon, gut tissue, skin scrape, or bone marrow aspirate. Tissue samples include, but are not limited to, biopsied or surgically removed tissue, including tissues that are unfixed, frozen, or fixed (e.g., in formalin or paraffin).

Cattle: Any of various chiefly domesticated mammals of the genus *Bos*, including cows, steers, bulls and oxen, often raised for meat and dairy products.

cDNA (complementary DNA): A piece of DNA lacking internal, non-coding segments (introns) and transcriptional regulatory sequences. cDNA can also contain untranslated regions (UTRs) that are responsible for translational control in the corresponding RNA molecule. cDNA is synthesized in the laboratory by reverse transcription from mRNA extracted from cells.

Degenerate variant: A degenerate variant of a primer includes sequences that have altered nucleic acid sequences but retain their ability to bind to the target sequences and identify or amplify the fungal target with sufficient specificity. In some embodiments, no more than 1, 2, 3 or 4 nucleic acids are changed, or the primer retains at least 85%, 90%, 92% or 95% sequence identity to the original sequence. Degenerate sequences also include primer sequences to which additional sequences have been added, while still retaining the specificity of the primer.

A degenerate variant of an *Aspergillus* primer sequence includes sequences that have altered nucleic acid sequences, but which retain their ability to identify *Aspergillus* sequences, for example a sequence from a particular *Aspergillus* species.

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases (adenine, cytosine, guanine and thymine) bound to a deoxyribose sugar to which a phosphate group is attached. Triplets of nucleotides (i.e., "codons") code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. For instance, it is appropriate to generate probes or primers from the reverse complement sequence of the disclosed nucleic acid molecules.

Encode: A polynucleotide is said to encode the polypeptide if, in its native state or when manipulated by methods well known to those skilled in the art, it can be transcribed and/or translated to produce the mRNA and/or the polypeptide or a fragment thereof. The antisense strand is the complement of such a nucleic acid, and the encoding sequence can be deduced therefrom.

Feed or food: food source humans or animals, for example food for livestock. In sum and body months, feed is pasture, hay, or grain, ground or whole. In general, food is material, usually of plant or animal origin, that contains or consists of essential body nutrients, such as carbohydrates, fats, proteins, vitamins, or minerals, and is ingested and assimilated by an organism to produce energy, stimulate growth, and maintain life.

Fungus: any living, single-cellular or multi-cellular organism belonging to the kingdom Fungi. Most species are characterized by a lack of chlorophyll and the presence of chitinous cell walls. Some fungi are multinucleated. Representative examples of fungal species include, but are not limited to, *Aspergillus fumigatus, A. niger, A. flavus, A. terreus, A. nidulans, Candida albicans, C. glabrata, C. tropicales, C. krusei, C. parapsilosis, C. neoformans, Fusarium solani, Trichosporon asahii, T mucoides, Mucor racemosus, Scedosporium* spp., *Epicoccum* spp. Pseudallescheria spp. and *Penicillium* spp.

Isolate: A biological component (such as a nucleic acid molecule) that has been substantially separated or purified away from other biological components in the cell of the organism in which the component naturally occurs, i.e., other chromosomal and extra-chromosomal DNA and RNA, proteins and organelles. Nucleic acids that have been isolated include nucleic acids purified by standard purification methods. The term also embraces nucleic acids prepared by recombinant expression in a host cell as well as chemically synthesized nucleic acids.

Jejunal hemorrhage syndrome (JHS): A newly-emerging disease that primarily affects dairy cows across the United States. JHS (also known as dead gut syndrome and hemorrhagic bowel syndrome) usually is characterized by a sudden drop in milk production in dairy animals, but has also been observed in grazing beef cattle. Affected animals exhibit colitis or ileitis, and develop diarrhea which later turns black. Death is due to anemia and obstructed bowel, and affected animals generally are dead within 24 hours of exhibiting symptoms. On necropsy, animals with JHS have distinct sections of the jejunum that are distended with large amounts of blood.

JHS can affect both distal and proximal portions of the jejunum, however proximal sites are the most common. The disease is characterized by the formation of one or more firmly-attached jejunal blot clots. These clots typically range from 6-24 inches long, and an unattached clot may extend proximally to the duodenum. The site of hemorrhage is between the muscularis mucosa and submucosa, beginning as a blood blister between these regions that expands and tears away the glandular mucosa from underlying tissues. Lacteals (origin of lymphatic drainage from the gut) also may be engorged with blood.

First described in 1991, JHS incidence is increasing and is responsible for at least 2% of the deaths of dairy animals in the United States. The cause of JHS is unknown; many potential causes have been investigated and discarded. Agents which do not play an etiologic role include parasitism, BVD, *coccidia, salmonella*, coagulopathies, intestinal foreign bodies, physical obstructions and deformities including volvulus and intussuception. Furthermore, analyses of diets, ages of cow, levels of milk production and a full spectrum of blood chemistry and biochemical assays have failed to reveal a consistent clinical correlate to JHS.

Nucleic Acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Nucleotide: This term includes, but is not limited to, a monomer that includes a base linked to a sugar, such as a pyrimidine, purine or synthetic analog thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Open reading frame: A series of nucleotide triplets (codons) coding for amino acids without any internal termination codons. These sequences are usually translatable into a peptide.

Primers: Nucleic acid primers can be readily prepared based on the nucleic acid molecules provided in this disclosure. Primers are short nucleic acid molecules, preferably DNA oligonucleotides 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Methods for preparing and using primers are described, for example, in Sambrook et al. (*Molecular Cloning: A Laboratory Manual*, CSHL, New York, 1989), Ausubel et al. (*Current Protocols in Molecular Biology*, Greene Publ. Assoc. and Wiley-Intersciences, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, 1991, Whitehead Institute for Biomedical Research, Cambridge, Mass.). One of ordinary skill in the art will appreciate that the specificity of a particular probe or primer increases with its length. Thus, in order to obtain greater specificity, primers can be selected that comprise at least 17, 20, 23, 25 or more consecutive nucleotides of fungal nucleotide sequences.

Ruminant: Any of various hoofed, even-toed, usually horned mammals of the suborder Ruminantia, such as cattle, sheep, goats, deer, and giraffes, characteristically having a stomach divided into four compartments and chewing a cud consisting of regurgitated, partially digested food.

Sequence identity: The similarity between two nucleic acid sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith & Waterman, *Adv. Appl. Math.*, 2: 482, 1981; Needleman & Wunsch, *J. Mol. Biol.*, 48: 443, 1970; Pearson & Lipman, *Proc. Natl. Acad. Sci. USA*, 85:

2444, 1988; Higgins & Sharp, *Gene,* 73: 237-244, 1988; Higgins & Sharp, CABIOS 5: 151-153, 1989; Corpet et al., *Nuc. Acids Res.,* 16, 10881-10890, 1988; Huang et al., *Computer Appls. in the Biosciences.* 8, 155-165, 1992; and Pearson et al., *Meth. Mol. Bio.,* 24, 307-331, 1994. Altschul et al. (*J. Mol. Biol.,* 215:403-410, 1990) present a detailed consideration of sequence alignment methods and homology calculations.

The NCBI Basic Local Alignment Search Tool (BLAST) (Altschul et al., *J. Mol. Biol.,* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. and in Tijssen (*Laboratory Techniques in Biochemistry and Molecular Biology—Hybridization with Nucleic Acid Probes Part I*, Chapter 2, Elsevier, N.Y. (1993)).

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

DESCRIPTION OF EMBODIMENTS

Provided here in as a method of detecting or quantifying or identifying a fungal species in a sample. The method includes amplifying a fungal nucleic acid sequence present in the sample using a primer selected from the group consisting of: SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16, observing or measuring the amplified nucleic acid sequence, and thereby detecting or quantifying or identifying the fungal species in the sample.

Also provided herein is a method of diagnosing JHS in a subject. The method includes amplifying a fungal nucleic acid sequence present in a biological sample from the subject using a primer selected from the group consisting of: SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16, observing or measuring the amplified nucleic acid sequence, and thereby diagnosing JHS in the subject.

Another aspect of the disclosure is a second method of diagnosing JHS in a subject. The method includes amplifying a fungal nucleic acid sequence present in a sample of the subject's feed or food using a primer selected from the group consisting of: SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16, observing or measuring the amplified nucleic acid sequence, and thereby diagnosing JHS in the subject.

Yet another aspect is a method of detecting or measuring fungal contamination in a feed or food sample. The method includes amplifying a fungal nucleic acid sequence present in a feed or food sample using a primer selected from the group consisting of: SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16, observing or measuring the amplified nucleic acid sequence, thereby detecting or measuring fungal contamination in the feed or food sample.

Also provided herein is an isolated nucleic acid that includes a nucleic acid sequence at least 85% identical to the nucleic acid sequence set forth as SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16.

Still another aspect is a kit for detecting in measuring fungal contamination in a biological or feed or food sample. The kit includes a container and a primer selected from the group consisting of: SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16.

Yet another aspect is a kit for diagnosing jejunal hemorrhage syndrome. The kit includes a container and a primer selected from the group consisting of: SEQ. ID NO 5, SEQ. ID NO 6, SEQ. ID NO 7, SEQ. ID NO 8, SEQ. ID NO 9, SEQ. ID NO 10, SEQ. ID NO 11, SEQ. ID NO 12, SEQ. ID NO 13, SEQ. ID NO 14 or SEQ. ID NO 16.

A. Overview of Several Embodiments

Provided herein is a simple, rapid method of detecting, quantifying, or identifying a fungal species in a sample. The method is useful for detecting fungal contamination in a sample, e.g. a biological sample from a subject suspected of having JHS. In one embodiment of the disclosure, the method includes amplifying a fungal nucleic acid sequence present in the sample using a primer selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 16; and observing an amplified fungal nucleic acid sequence to thereby detect the fungal species in the sample. In some examples of its embodiments, the method further includes amplifying a fungal nucleic acid sequence present in the sample using a primer selected from the group consisting of: SEQ ID NO: 1, SEQ ID NO: 2, SEQ ID NO: 3, SEQ ID NO: 4, and SEQ ID NO: 15.

In certain examples of the embodiment, the sample is a feed sample, such as a cattle feed sample. In other examples of the embodiment, the sample is a biological sample from a subject. In particular examples of the embodiment, the subject is an animal, for example a ruminant. In even more particular examples of the embodiment, the subject is suspected of having jejunal hemorrhage syndrome.

Observing the amplified nucleic acid sequence can also include measuring the amplified nucleic acid sequence. The method can further include quantifying the amplified fungal nucleic acid sequence. Still further, the method can include identifying a detected fungal species by correlating the observed fungal nucleic acid sequence with a fungal species.

Also provided herein is a method of diagnosing jejunal hemorrhage syndrome in a subject, comprising amplifying a fungal nucleic acid sequence present in a biological sample from the subject using a primer selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 16; and observing an amplified fungal nucleic acid sequence to thereby diagnose jejunal hemorrhage syndrome in the subject. In some examples of the embodiment, the method of further includes amplifying a fungal nucleic acid sequence present in the sample using a primer selected from the group consisting of: SEQ ID NO: 1, SEQ ID NO: 2, SEQ ID NO: 3, SEQ ID NO: 4, and SEQ ID NO: 15.

In still other embodiments of this method, observing the amplified fungal nucleic acid sequence can include measuring the amplified fungal nucleic acid sequence.

A further embodiment of the disclosure is a second method of diagnosing jejunal hemorrhage syndrome in a subject. The method includes amplifying a fungal nucleic acid sequence present in sample of the subject's feed using a primer selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 16; and observing the amplified nucleic acid sequence to thereby diagnose jejunal hemorrhage syndrome in the subject. In some examples of the embodiment, the method also includes amplifying a fungal nucleic acid sequence present in the sample using a primer selected from the group consisting of: SEQ ID NO: 1, SEQ ID NO: 2, SEQ ID NO: 3, SEQ ID NO: 4, and SEQ ID NO:15.

Yet another embodiment of the disclosure is a method of detecting or measuring fungal contamination in a feed sample. The method includes amplifying a fungal nucleic acid sequence present in the feed sample using a primer selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 16; and observing or measuring the amplified nucleic acid sequence to thereby detect fungal contamination in the feed sample. In some examples of the embodiment, the method also includes amplifying a fungal nucleic acid sequence present in the sample using a primer selected from the group consisting of: SEQ ID NO: 1, SEQ ID NO: 2, SEQ ID NO: 3, SEQ ID NO: 4, and SEQ ID NO: 15. In certain examples, the feed is livestock food or feed, and in a specific embodiment the food or feed sample is cattle feed.

Also disclosed herein is an isolated nucleic acid that includes a nucleic acid sequence at least 85% identical to a the nucleic acid sequence set forth as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:16. In some embodiments, the nucleic acid includes a nucleic acid sequence at least 90% identical to a the nucleic acid sequence set forth as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:16. In certain embodiments, the nucleic acid includes a nucleic acid sequence at least 95% identical to a the nucleic acid sequence set forth as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:16. In particular embodiments, the nucleic acid includes a nucleic acid sequence set forth as SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:16.

Further embodiments of the disclosure are kits for detecting and measuring fungal contamination in a feed sample. The kit comprises a container and a primer selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO:13, SEQ ID NO:14, and SEQ ID NO:16. In certain examples, the kit also includes a primer selected from the group consisting of: SEQ ID NO: 1, SEQ ID NO: 2, SEQ ID NO: 3, SEQ ID NO: 4, and SEQ ID NO: 15. In particular examples, the kit further includes a preservative, and in still more particular examples, the kit also includes instructions for using the kit.

Still further embodiments of the disclosure are kits for diagnosing jejunal hemorrhage syndrome. The kits include a container and a primer selected from the group consisting of: SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, and SEQ ID NO: 16. In certain examples, the kit also includes a primer selected from the group consisting of: SEQ ID NO: 1, SEQ ID NO: 2, SEQ ID NO: 3, SEQ ID NO: 4, and SEQ ID NO: 15. In particular examples, the kit further includes a preservative, and in still more particular examples, the kit also includes instructions for using the kit.

B. Jejunal Hemorrhage Syndrome is Caused by *Aspergillus*

Disclosed herein is the finding that jejunal hemorrhage syndrome in dairy cattle is caused by *A. fumigatus*. Prior to this discovery, a number of potential causes of JHS were been investigated and discarded. Agents that have been found not to play an etiologic role include parasites, BVD, coccidia, *salmonella*, coagulopathies, intestinal foreign bodies, physical obstructions, and deformities including volvulus and intussuception. Furthermore, analyses of diets, ages of cow, levels of milk production and a full spectrum of blood chemistry and biochemical assays failed to reveal a consistent clinical correlate to JHS.

The bacterium *Clostridium perfringens* was previously associated with JHS because it was isolated from fecal samples from a number of cows with JHS. However, it is likely that proliferation of *C. perfringens* is not part of the primary disease process in cows with JHS, but occurs as a secondary response to the disease.

C. perfringens is ubiquitous in dairy cattle (Songer, "Clostridial enteric diseases of domestic animals." *Clin. Microbiol. Rev.*, 9:216-234 (1996); Jensen, et al., "Mycosis in the stomach compartments of cattle," *Acta Vet. Scand.*, 30:409-423 (1989)), and immunization against *Clostridium* species does not protect animals from JHS.

By contrast, *Aspergillus* either was not detected or was detected at extremely low levels in control cows, significantly, it was detected in the tissues and blood of every cow with JHS (see Example 2). Several JHS cows exhibited invasive aspergillosis, as indicated by the presence of *Aspergillus* DNA in blood and liver tissue. In addition, samples of feed stocks fed to cows that developed JHS were found to be contaminated with *Aspergillus*. Thus, infection with *Aspergillus* species likely is the cause of JHS.

C. Methods of Detecting Fungal Species in Samples and Feed

Methods are provided for testing samples, such as biological samples and feed samples, for fungal contamination. Such methods are useful for confirming a diagnosis of JHS in an animal suspected to have JHS and additionally for identifying the source of fungal contamination in an animal suffering from JHS. Furthermore, such methods can be used in assessing the risk of developing JHS in an animal or group of animals. For example, the method can be used to determine whether a given herd of cattle is at risk of developing JHS from a particular store of feed. The method is also useful for determining the fungal load in other samples, e.g., human food supplies, medical supplies, or determining surface contamination with fungal species, for example contamination of a household surface.

In some embodiments, the method includes amplifying a fungal nucleic acid sequence from a sample. Appropriate samples include any conventional environmental or biological sample, including samples obtained from a human or animal subject, for instance a cow suspected of having JHS. Appropriate samples also include animal feed, for example pasture, hay, or grain, ground or whole. Suitable samples also include, but are not limited to, body fluid samples, such as blood, derivatives and fractions of blood (e.g., serum, plasma), tears, milk, surface washings, urine, cerebrospinal fluid, pus, sputum, bronchoalveolar lavage, ocular fluid, saliva, fecal fluid. Suitable samples also include, but are not limited to tissue samples, such as muscle, nerve, epidermal, connective tissue, liver, intestine, lymph node, cotyledon, or gut tissue, skin scrapes, or bone marrow aspirates. Tissue samples also include, but are not limited to, biopsied or surgically removed tissue, including tissues that are unfixed, frozen, or fixed in formalin or paraffin.

In some embodiments, nucleic acids are isolated from the sample. DNA or RNA can be extracted using standard methods. For example, rapid DNA preparation can be performed using a commercially available kit (e.g., Qiagen Tissue Kit, Qiagen, Inc., Valencia, Calif.). In some embodiments, the DNA preparation technique is selected to yield a nucleotide preparation that is accessible and amenable to nucleic acid amplification.

In one specific, non-limiting example, fungal primers (e.g., SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16) are used to amplify fungal sequences from the sample. In some embodiments of the example, additional fungal primers (e.g., SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16) are used to confirm the presence of the fungal sequence, quantify the amount of fungal sequence present in the sample, or identify the fungal species present in the sample. In some embodiments of the example, sequence analysis is used to determine the presence or identity of the fungal species.

D. Methods of Diagnosing JHS

Methods are provided for detecting or diagnosing JHS in an subject. Some such methods include amplifying a fungal nucleic acid sequence from a biological sample from the subject, particularly an animal suspected of having JHS. The methods used for detecting or diagnosing JHS in an animal are the same as those described in section IIIC, above.

E. Variant Primer Sequences

One of skill in the art will recognize that the DNA sequence of the primers disclosed may be varied, while still producing functional fungal primers. Nucleotide sequences which are derivatives of those specifically disclosed herein and that differ from those disclosed by the deletion, addition, or substitution of nucleotides while still functioning as primers that amplify fungal sequences are comprehended by this disclosure. In some embodiments of the disclosure, a variant fungal primer can have, for example 85%, 90%, or 95% sequence identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 16.

In addition, unique sequences (~18-30 bp each) to several different pathogenic fungal species (*Aspergillus fumigatus, A. niger, A. flavus, A. terreus, A. nidulans, Candida albicans, C. glabrata, C. tropicales, C. krusei, C. parapsilosis, C. neoformans, Fusarium solani, Trichosporon asahii, T mucoides, Mucor racemosus, Scedosporium* spp., *Epicoccum* spp. *Pseudallescheria* spp. and *Penicillium* spp.) can be developed based on highly polymorphic genomic regions of the ITS-1, ITS-2 and mitochondrial DNA sequences of these organisms. Primers are selected that specifically hybridize to these regions that identify and distinguish between these species. These primers are of use in identifying the infectious agent in a subject with JHS. Such a determination is useful in selecting a therapy for a subject with JHS.

F. Kits

In some embodiments, the oligonucleotide primers disclosed herein are supplied in the form of a kit for the detection of fungal contamination in feed or biological samples, or for the diagnosis of JHS. In such a kit, one or more of the oligonucleotide primers is provided in one or more containers. In some kits, an oligonucleotide primer is provided suspended in an aqueous solution; in other kits, the oligonucleotide primer can be supplied as a freeze-dried or lyophilized powder. Some kits include tagged primers, for example TaqMan primers, for the quantification of the fungal sequence(s). The container(s) in which the oligonucleotide(s) are supplied may be any conventional container that is capable of holding the supplied form, e.g., a microfuge tube, an ampoule, a bottle, or an envelope. In some embodiments of the disclosure, primers are provided in pre-measured, single-use forms in individual tubes or equivalent containers. In particular embodiments, the containers also include buffers, preservatives, or other reagents. In particular examples, the sample to be tested is added directly to the container, and amplification is carried out directly. In some embodiments of the disclosure, the kit also includes a container and reagents for the subsequent sequence analysis of the amplified sequence.

In one particular and non-limiting example, the kit includes a container, instructions for use, sample tubes for sample collection, and a suitable preservative for the preservation of the sample(s), such as formaldehyde, formalin, ethanol, a protease inhibitor, ice, dry ice, liquid nitrogen, etc. Particular embodiment of that kit also includes shipping envelopes for samples, protective packaging for samples, and labels. Such a kit would be used to collect samples, whereupon the kit would be returned to a laboratory and processed using the fungal primers disclosed herein. Such a kit would permit the detection of fungal species, determination of fungal abundance, fungal species identification, and determination of abundance of a specific fungal species in the sample.

In another particular, non-limiting example, the kit comprises a container, instructions for using the kit, and primers for one or more fungal species to enable the user to simultaneously assess abundance of one or more different fungal species, thermocycling plates, and, optionally, optical film. A user of the kit first purifies a DNA sample, for example, using a commercial kit. Amplification is performed using a thermocycler, such as the ABI7700 (Applied Biosystems, Foster City, Calif.).

G. Microarray Chips

The primers disclosed herein can be provided on a microarray chip and used to detect, quantify, or identify fungal species in a sample, or to diagnose JHS in an animal or other subject. In a specific, non-limiting example, unique sequences (for example, approximately 70 bp each) to several different pathogenic fungal species (for instance, *Aspergillus fumigatus, A. niger, A. flavus, A. terreus, A. nidulans, Candida albicans, C. glabrata, C. tropicales, C. krusei, C. parapsilosis, C. neoformans, Fusarium solani, Trichosporon asahii, T mucoides, Mucor racemosus, Scedosporium* spp., *Epicoccum* spp. *Pseudallescheria* spp. and *Penicillium* spp.) are developed based on highly polymorphic genomic regions of the ITS-1, ITS-2 and mitochondrial DNA sequences of these organisms. In some aspects of the disclosure, variant sequences are 85%, 90% or 95% identical to the ITS-1, ITS-2 and mitochondrial DNA sequences of these organisms.

Optionally, an appropriate negative control DNA (for example, *S. cerevesiae*) sequence is also included. In particular examples, the $T_m$ of each sequence is designed to be about from about 73-83° C., or more particularly, from about 75-80° C., or about 78° C. Sequences are affixed to Affymetrix (Santa Clara, Calif.) microarray chips and then screened for specificity by applying purified DNA from each of the test species noted above to the slide.

To test the efficacy of the chip in detecting a fungal infection, control animals, for example steers and broiler chickens, are infected with fungi, and blood samples are taken for a period post-infection, for example, for two weeks. DNA is purified from the control blood samples and then screened using the fungal microarray chip.

In some embodiments, such a microarray chip is provided as a kit that includes a container, the chip, and instructions for use.

H. Methods of Testing the Efficacy of an Antifungal Treatment

The methods described herein are also useful for testing the efficacy of an antifungal treatment. For example, the method can be used to test a sample from an animal (e.g., a rat, mouse, chicken, beef cow, dairy cow, pig, or sheep) that has been infected with a pathogenic fungus (e.g., *Aspergillus fumigatus*). The method of section III.C (above) can be used to detect the presence of fungal DNA in tissues and blood samples, and the efficacy of various antifungal agents (e.g., amphotericin B, griseofulvin, ketoconazole, nystatin, miconazole, or putative novel anti-mycotics) on the tissue levels and blood levels of fungal DNA.

The method also can be used to monitor the efficacy of feed or food additives or preservatives on the accumulation of fungi in the feed or food over time (e.g., during feed storage).

EXAMPLES

Example 1

Methods

A. Sample Collection

Samples from nine cows which developed JHS or abomasal hemorrhage (AH) and from several negative control cows were collected. Details of the cases are included in Table 2. Due to the epidemiological nature of the study, consistent samples were not recovered from each farm where JHS was diagnosed. Instead, a mixture of blood, feed and tissues samples were submitted. Tissue samples included gut wall, mesenteric lymph node, cotyledon and liver. Samples from the gut region where hemorrhage occurred were also submitted. The negative control cow samples were blood samples taken from healthy cows (n=14) and three non-JHS dead cows at Pacific Northwest dairies.

B. DNA extraction and SybrGreen analysis

DNA was extracted from blood, tissues and feeds using the Qiagen QIAmp DNA mini kit. Percent recovery of DNA via the Qiagen method was 80%. A 1 μl sample of DNA was combined with SybrGreen PCR reagents, forward and reverse primers to bring the final volume to 25 μl. A standard curve of *A. fumigatus* genomic template DNA (Source: Dr. Francoise Symoens, Scientific Institute of Public Health, Brussels, Belgium) was conducted in all assays. *A. fumigatus* "genomic units" were calculated based on an *A. fumigatus* genome size of 27 Mb. A genomic unit is equivalent to one ITS-1 region in a fungal genome. There are as many as 100 or more copies of ITS-1 domains in one genome. Hence, the fungal load is estimated in units of GU/100.

C. Semi-Quantitative Pan-Fungal Analysis

This method tested for the presence of fungal DNA in DNA extracted from a biological sample. There are reported to be over 100,000 fungal species. This method was used to test for the presence of any of these fungal species, making use of the high degree of conservation which exists in the sequence of the 18S ribosomal gene across species (see FIG. 1).

The method used the following primers:

F1; AGGGATGTATTTATTAGATAAAAAATCAA    (SEQ. ID NO: 1)

R1; CGCAGTAGTTAGTCTTCAGTAAATC    (SEQ. ID NO: 2)

to amplify the fungal 18S ribosomal subunit DNA using the following thermocycling conditions:

| | |
|---|---|
| Denaturation: | 95° C., 30 sec |
| Anneal: | 52° C., 30 sec |
| Extension: | 72° C., 30 sec |
| 38 cycles | |

The reaction mixture consists of:

| | |
|---|---|
| DNA template | 10 μl |
| dNTPs | 0.5 μl |
| F1 (10 pmoles/ul) | 0.5 μl |
| R1 (10 pmoles/ul) | 0.5 μl |
| Promega ® Buffer | 2.5 μl |
| MgCl$_2$ | 2.5 μl |
| | (final concentration 2.5 mM MgCl$_2$) |
| Promega Taq Polymerase | 0.5 μl |
| Water | 8.0 μl |
| Total | 25 μl |

These primer sequences (e.g., F1 and R1) result in a product of 743 base pairs and were developed by Jaeger et al., ("Rapid detection and identification of *Candida, Aspergillus,* and *Fusarium* species in ocular samples using nested PCR," *J. Clin. Microb.*, 38:8, 2902-2908) (2000)).

Following completion of the first PCR reaction with F1 and R1, the identity of the fungal DNA was confirmed employing nested PCR primers using the first 743 bp PCR product as a template. The two nested primers (F2 and R2) were:

F2: 5'-CCAATGCCCTTCGGGGCTCCT (SEQ. ID NO: 3)

R2: 5'-CCTGGTTCCCCCCACAG (SEQ. ID NO: 4; see FIG. 1 for positions). The thermocycling conditions used for the nested PCR analysis are:

| | |
|---|---|
| Denaturation: | 95° C., 30 sec |
| Anneal: | 66° C., 30 sec |
| Extension: | 72° C. |
| 40 cycles | |

The reaction mixture consists of:

| | |
|---|---|
| DNA template | 1.0 μl |
| | (from first PCR reaction) |
| dNTPs | 0.5 μl |
| F2 (10 pmoles/ul) | 0.5 μl |
| R2 (10 pmoles/ul) | 0.5 μl |
| Promega Buffer | 2.5 μl |
| MgCl$_2$ | 2.5 μl |
| | (final concentration 2.5 mM MgCl$_2$) |
| Promega Taq Polymerase | 0.5 μl |
| Water | 19.0 μl |
| Total | 25 μl |

These primers produced a PCR product of 520 bp, and will amplify sequences from many fungal genera.

D. Quantitative Analysis of Fungal Burden

Fungi are ubiquitous, hence, testing for a common fungus (e.g., using the method from section C, above), often produces a positive result. A more important test is to assay the amount of fungus present in the sample, as the amount of fungus (the fungal load or fungal burden) is important to clinical outcome. Thus fungal burden can be assessed using the following "quantitative" fungal load assay.

The method uses Sybr-Green (Molecular Probes, Eugene, Oreg.) real-time technology. Sybr-Green is a dye that binds to DNA and fluoresces when it binds. Primers were developed that amplify a 60 bp fragment of the 18S sequence. The accumulation of Sybr-Green fluorescence is monitored over time using an Applied Biosystems (Foster City, Calif.) 7700 real-time thermocycler. The two 18S ribosomal primers are:

F3: 5'-GAAGAACGCAGCGAAATGC (SEQ. ID NO: 5)

R3: 5'-CCAACACACAAGCCGTGCT (SEQ. ID NO: 6)

Reaction conditions are:

| | |
|---|---|
| Denaturation: | 95° C., 15 sec |
| Annealing and Extension: | 60° C., 60 sec |
| Data collection | 83° C., 15 seconds |
| 40-45 cycles | |

Sybr-Green amplification reactions are as follows:

| | |
|---|---|
| DNA sample | 1-14.1 μl |
| | (>100 fmoles genomic DNA) |
| Sybr-Green buffer | 2.5 μl |
| MgCl$_2$ | 3 μl |
| dNTPs | 2 μl |
| AmpliTaq Gold | .125 μl |
| AmpErase | .25 μl |
| Primer F3 | 1.5 μl |
| | (Primer stock is 5 μM) |
| Primer R3 | 1.5 μl |
| | (Primer stock is 5 μM) |
| Water | to bring total volume to 25 μl |

This method is useful for the quantitative analysis of fungal load in, for example, food, feed, blood, tissue, sputum, ocular, air and household samples.

E. Amplification of the Polymorphic ITS-1 and ITS-2 Regions of Fungal DNA for Species Identification The 18S, 5.8S and 28S ribosomal genes in fungal species are highly conserved (e.g., relatively few differences in DNA sequences are present). However, the regions between these genes (ITS-1 and ITS-2, see FIG. 1) are polymorphic. Hence, sequence information from these regions can be used to identify specific fungal species involved in an infection or contamination. To obtain this sequence information, the polymorphic ITS-1 and ITS-2 regions are amplified and then sequenced using conventional sequencing methods.

This method uses PCR primer sequences that amplify fungal ITS-1 and ITS-2 regions. These methods are non-quantitative, and use a primary PCR analysis and a nested (confirmatory) analysis. The primary analysis uses the following primers:

F4: 5'-GGTGAGGCCTTCGGACTG
(SEQ. ID NO: 7; 25 pmol/μl)

R4: 5'-CCTCCGCTTATTGATATGCTTAAG
(SEQ. ID NO: 8; 25 pmol/μl)

This primer set amplifies fungal DNA samples using the 3'-end of the 18S ribosomal gene and the 5'-end of the 28S gene. Genomic template from DNA samples isolated from feed, food, blood, tissue or air is amplified with this method. The cycling program used is:

| | |
|---|---|
| Denaturation: | 95° C., 30 sec |
| Anneal: | 56° C., 30 sec |
| Extension: | 72° C., 30 sec |
| 35 cycles | |

The PCR reaction mixture is the same as used in section C (above) for genomic template DNA. The 660 bp PCR product is then used as template in a nested PCR analysis to confirm that the 660 bp product is truly the product of fungal DNA. To accomplish this, the product is placed in a thermocycling program using the following nested primers which generates a 538 bp fragment:

```
F5: 5'-CGTAACAAGGTTTCCGTAGGTG
    (SEQ. ID NO: 9; 25 pmol/µl)

R5: 5'-GCGGGTATCCCTACCTGATC
    (SEQ. ID NO: 10; 25 pmole/µl)
```

The cycling program used is:

| Denaturation: | 95° C., 30 sec |
| --- | --- |
| Anneal: | 62° C., 30 sec |
| Extension: | 72° C., 30 sec |
| 35 cycles | |

The reaction mixture is the same as that used for the nested analysis from section C (above).

F. A Second Method for Amplification of Polymorphic ITS-1 and ITS-2 Regions of Fungal Samples A second single-reaction method permits the amplification of large quantities of polymorphic fungal DNA sequences which then can be sequenced and used for fungal species identification. The PCR method used in this example employs the following primers:

```
Sybr-ITS-F1:    5'-AACCTCCCACCCGTGTCTATC
    (SEQ. ID NO: 11; 5 µM stock)

R4:             5'-CCTCCGCTTATTGATATGCTTAAG
    (SEQ. ID NO: 8; 25 pmol/µl)
```

The reaction mixture was identical to that outlined in section C except that an annealing temperature of 58° C. is used and 40 cycles were used for amplification. This method yielded a fragment of about 500 bp that was excised and purified from an agarose gel and then sequenced to identify the species of fungus in the original sample.

G. A Method for Determination of the Abundance of *Aspergillus fumigatus* DNA in Biological Specimens This method is a Sybr-Green-based method that uses primers that selectively amplify *A. fumigatus* genomic DNA. The primers are based on the unique polymorphic sequences of *A. fumigatus* DNA found in the ITS-1 region of the *A. fumigatus* genome. The primers are:

```
Sybr-ITS-F1:    5'-AACCTCCCACCCGTGTCTATC
    (SEQ. ID NO: 11; 5 µM stock)

Sybr-ITS-R1:    5'-GCGGCCGTCGAAACG
    (SEQ. ID NO: 12; 5 µM)
```

The Sybr-Green real-time PCR reaction is identical to the method outlined in section D, above.

H. Methods for Quantitation of other *Aspergillus* Genera in Biological Samples

This method is useful for quantifying infection by other members of the *Aspergillus* genera using the Sybr-Green approach. This approach is identical to the method of section G, except that primers specific for other *Aspergillus* species are used. Primer sequences are given below:

*Aspergillus flavus*

```
F: 5'-GCCGGAGACACCACGAAC
   (SEQ. ID NO: 13; 5 µM stock)

R: 5'-CGATACAATCAACTCAGACTTCACTAGA
   (SEQ. ID NO: 14; 5 µM stock)
```

*Aspergillus niger*

```
F: 5'-CCGAGTGCGGGTCCTTT
   (SEQ. ID NO: 15; 5 µM stock)

R: 5'-CCGAAGCAACAGGGTACAATAGA
   (SEQ. ID NO: 16; 5 µM stock)
```

I. Clostridial Toxin Genotyping

A multiplex PCR-based assay was adapted for simultaneous assay of five of the major clostridial exotoxin genes (α, β, ε, ι and enterotoxin). Methods were identical to those outlined by Meer and Songer ("Multiplex polymerase chain reaction assay for genotyping *Clostridium perfringen,*" *Am. J. Vet. Tes.*, 7:702-705 (1997)).

Example 2

Jejunal Hemorrhage Syndrome is caused by *Aspergillus fumigatus*

Described herein is the finding that JHS is associated with high levels of *A. fumigatus* in the gut, gut wall and blood. In human studies, *A. fumigatus* is recognized for its invasive properties and pathogenicity in immunocompromised patients. These data demonstrate that it has a similar potential in ruminants. However, more than 100,000 fungal species are known, and there are more than 100 *Aspergillus* species. Only a very small proportion of their ITS domains have been published. Hence, detection of *A. fumigatus* could include unrecognized (non-sequenced) fungal species. In addition, other predisposing factor(s), for example stress-induced immunoincompetence, may also contribute to the development of JHS.

A. Development of PCR Assay

Figure 1:
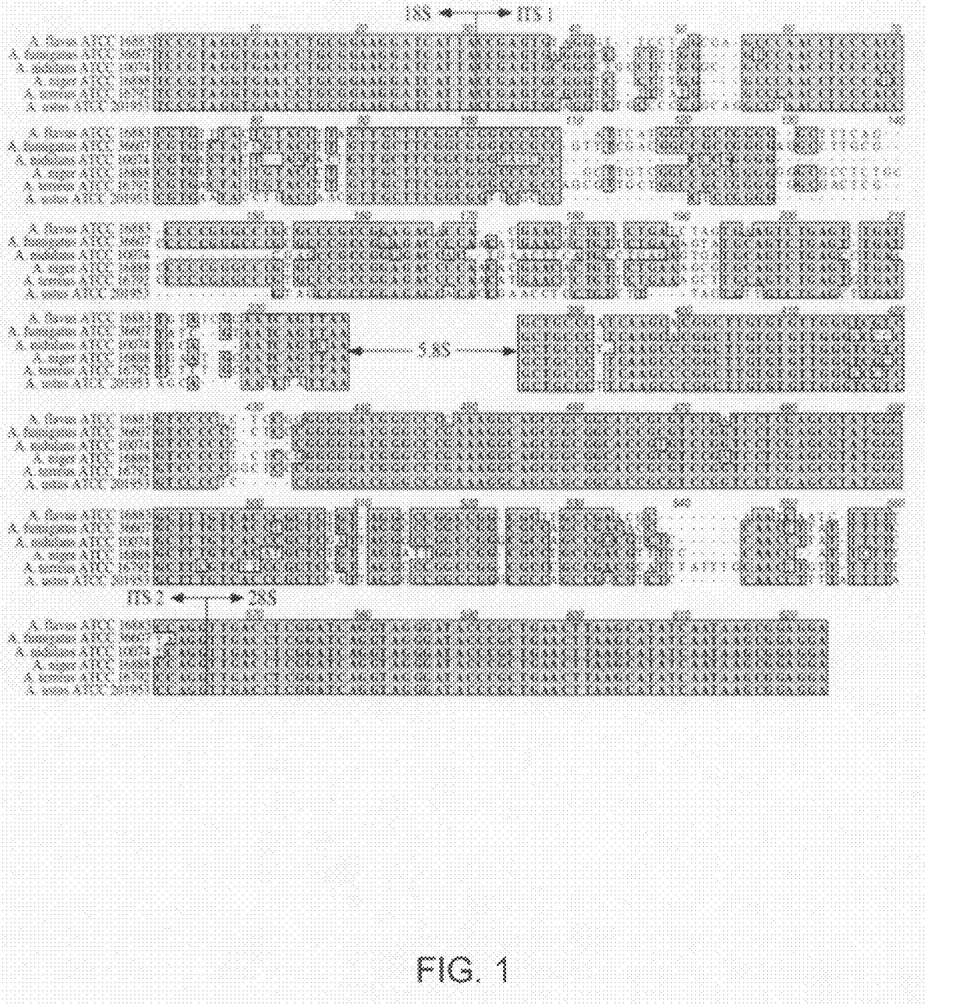
FIG. 1 is a diagram showing the ribosomal DNA gene cluster in fungi. The sequences provided from top to bottom are SEQ ID NOs: 17-22, respectively.
Figure 2:
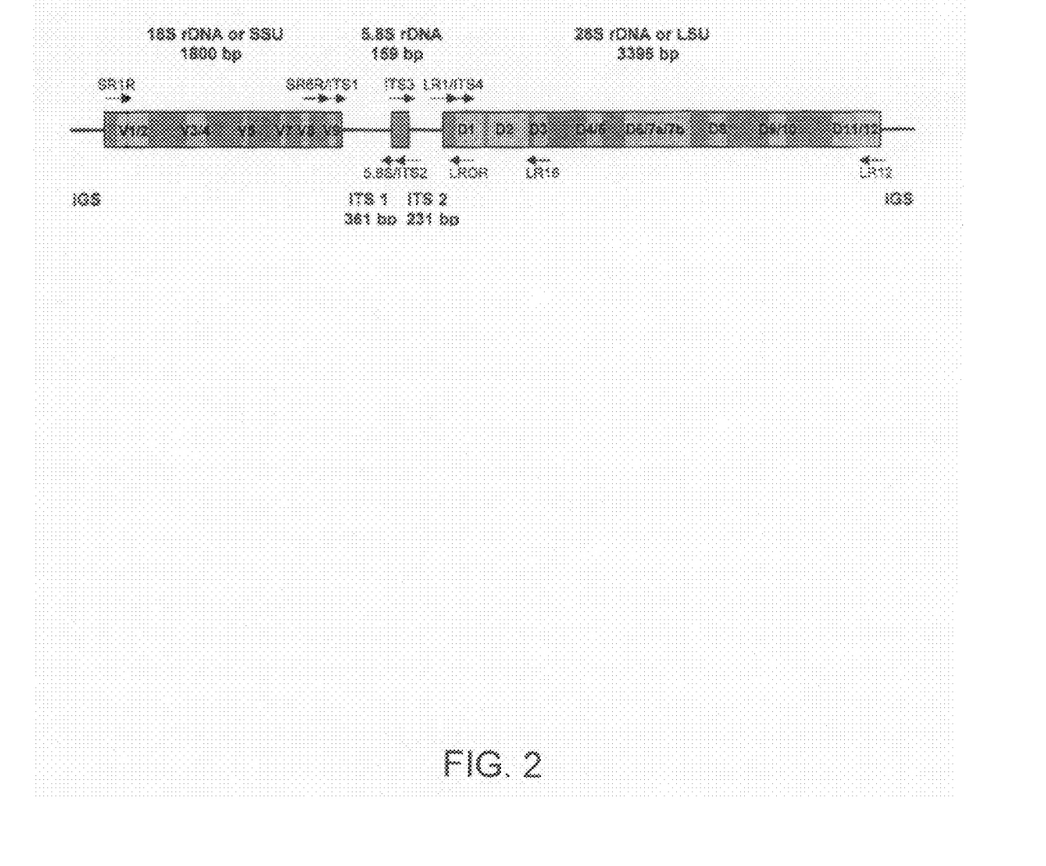
FIG. 2 is a diagram showing the ITS-1 and ITS-2 sequences of six *Aspergillus* species.
Figure 3:
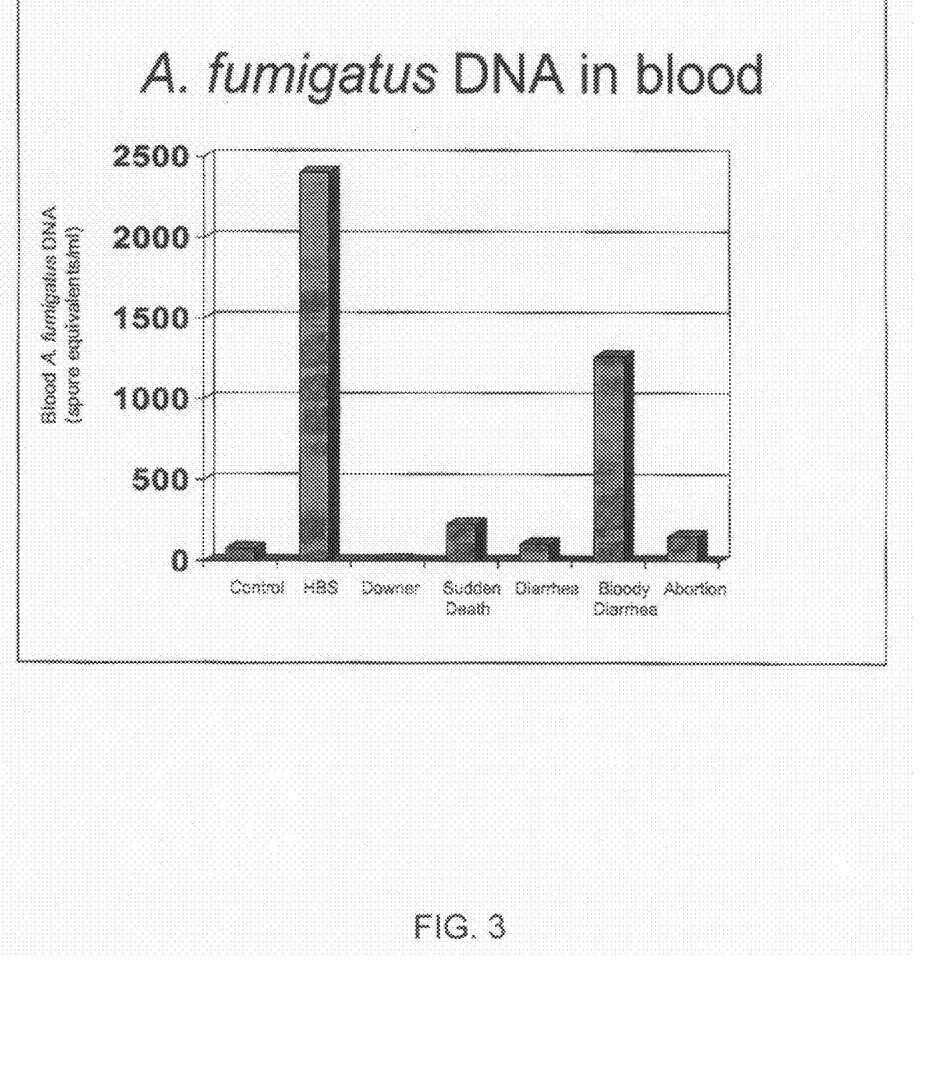
FIG. 3 is a graph showing results of testing for fungal DNA in blood samples.

To quantify *A. fumigatus* in feed, tissues and blood, a "real-time" quantitative PCR assay was developed. The assay was based on the sequences of the fungal ribosomal genes (FIG. 1). Three ribosomal genes (18S, 5.8S and 28S, respectively) border two variable internally-transcribed spacer (ITS) domains (designated as ITS-1 and ITS-2). The sequences within the ribosomal genes are highly conserved. However, sequences within the ITS-1 and -2 regions are not conserved (FIG. 2), and allowed design of primers which specifically bound to *A. fumigatus* genomic DNA in a thermocycler. A forward primer and a reverse primer were synthesized and used in the development of a SybrGreen assay for detection of *A. fumigatus* DNA in biological samples.

B. *A. fumigatus* Genomic Analysis of JHS Cows

Results of *A. fumigatus* genomic analysis from eight JHS cows, one abomasal hemorrhage (AH) cow and one AH gazelle are shown in Table 2. *A. fumigatus* was detected in 3 of 3 (3/3) feeds submitted for analysis. It was also detected in the gut contents (7/7), gut wall (5/5), and mesenteric lymph node (3/5). Invasive aspergillosis was indicated by detection of *A. fumigatus* DNA in blood (6/6) and in liver (1/1). One case of JHS was associated with a late-term abortion. Cotyledons from the case were sampled and also found to harbor *A. fumigatus*. Of interest, *A. fumigatus* DNA was also detected in two cases of abomasal hemorrhage (AH), one in a dairy cow and another in a Dama gazelle (Table 2).

Several negative control cows (e.g., non-JHS; n=17) were also processed and, of these, 14 tested negative for *A. fumigatus*. The remaining cows (n=3) contained very low levels of *A. fumigatus* DNA, near the detection limit of the assay (e.g., <0.02×10$^6$ *A. fumigatus* genomic units/ml of blood). These levels were 1/20$^{th}$ to 1/50,000$^{th}$ of the levels detected in JHS cows. Two of the negative control cows (which tested negative for *A. fumigatus*) were cows which had died from unknown causes at two different dairies. Both had exhibited rumen stasis and sudden death but did not have JHS.

A survey was conducted to identify the relationship between *A. fumigatus* and various diseases and causes of death in dairy cattle. A total of 208 blood samples were received from across the United States. Of these, *A. fumigatus* levels of 2400 *A. fumigatus* spore equivalents/ml were detected in blood samples from cows identified as having died from JHS. In contrast, blood samples from control (non-JHS death) cows had *A. fumigatus* spore equivalents of 75/ml (i.e., a 30-fold difference). Also of interest, *A. fumigatus* levels were elevated in bloody diarrhea cases.

C. Feed-Borne *Aspergillus fumigatus* Causes JHS

Local feeds were tested for the presence of *A. fumigatus*. Feed samples include mill run, ground corn, grass and corn silages and dried grass hay. Many were infected with *A. fumigatus*. Infection is not always visible (*A. fumigatus* on moist feed, e.g., corn, is dark blue-green). Hence, exposure to *A. fumigatus* may be common Various feed samples were tested for the presence of *A. fumigatus*; results are displayed in Table 1. It can be seen that *A. fumigatus* is prevalent in many substances used as animal feed or components therein.

TABLE 1

Presence of *A. fumigatus* in feed.

| Commodity | n | *Aspergillus fumigatus* positive | % positive | Mean spores/g | Range spores/g |
|---|---|---|---|---|---|
| Alfalfa | 4 | 3 | 75 | 1,171 | 0-4,360 |
| Beet pulp | 10 | 7 | 70 | 26,609 | 0-118,125 |
| Corn | 22 | 21 | 96 | 7,539 | 0-57,800 |
| Corn-barley mix | 5 | 5 | 100 | 33,156 | 945-79,650 |
| Corn silage | 19 | 15 | 79 | 139,845 | 0-1,304,169 |
| Distiller's dried grains | 10 | 4 | 40 | 11,516 | 0-75,625 |
| Grass silage | 12 | 3 | 25 | 6,390 | 0-67,890 |
| Soybean meal | 10 | 5 | 50 | 3,028 | 0-23,800 |
| TMR | 7 | 7 | 100 | 1,963 | 108-6,350 |
| Wheat mill run | 5 | 1 | 20 | 6,480 | 0-32,400 |
| Whole cottonseed | 12 | 4 | 33 | 12,804 | 0-121,500 |

D. Clostridial Toxins

Genotype analysis of five clostridial toxins indicated no correlation between JHS and toxin genes (Table 3). In JHS and AH cases, genes encoding toxins α and ε were detected in 3 of 9 analyses. Toxin genes ι and enterotoxin were not detected in any samples. The α and ε toxin genes were detected in blood (1/3), jejunal or abomasal clot (2/4) and GI wall (1/5). In negative control cows, the β toxin gene was detected in blood of 3 of 17 animals (Table 3). Of interest, two of the three negative control cows which harbored the *Clostridium* β-toxin gene had aborted.

TABLE 2

Detection of *A. fumigatus* DNA in samples of blood, tissues and feed recovered from cases of jejunal hemorrhage syndrome and abomasal hemorrhage[1]

| Case Location/ID | Diagnosis[2] | Blood | Gut wall | Gut contents |
|---|---|---|---|---|
| WA #1 | JHS | ++ | | |
| Idaho #1[3] | JHS | +++ | +++ | + |
| Idaho #2[3] | JHS | ++++ | +++ | +++ |
| Iowa Feeds[4] | JHS | | | |
| OSUCVM[5] | AH | | ++++ | ++++ |
| WA #2 | JHS | | +++++ | +++++ |
| Iowa Dairy #1[6] | JHS | ++++ | ++ | +++ |
| Iowa Dairy #2[6] | JHS | +++ | +++ | +++++ |
| Gazelle OR[7] | AH | | ++ | |
| WA #3 | JHS | +++++ | | |

| Case Location/ID | Mesenteric lymph node | Liver | On-site feeds | Cotyledon |
|---|---|---|---|---|
| WA #1 | | | +++ | |
| Idaho #1[3] | − | | | |
| Idaho #2[3] | + | | | |
| Iowa Feeds[4] | | | +++++ | |
| OSUCVM[5] | | +++ | | |
| WA #2 | ++ | | ++ | ++ |
| Iowa Dairy #1[6] | +++++ | | | |
| Iowa Dairy #2[6] | − | | | |
| Gazelle OR[7] | | | | |
| WA #3 | | | | |

[1]*A. fumigatus* levels were determined and reported as 0 (no detectable *A. fumigatus* DNA) and + to +++++ (low level to very high level). These correspond to *A. fumigatus* loads ranging from 0, 0.2-1, 1-5, 5-20, 20-100 and >100 × 10$^6$ *A. fumigatus* genomic units per g of tissue, per ml of blood or per ml of gut contents (−, +, ++, +++, ++++, and +++++, respectively).
[2]JHS (jejunal hemorrhage syndrome). AH (abomasal hemorrhage). All diagnoses were completed by veterinarians (Oregon State University, University of Idaho), National Animal Disease Center (Iowa State University) or by field veterinarians.
[3]Sample was provided by Dr. Bruce Anderson (University of Idaho).
[4]Feeds only were obtained from a farm which experienced JHS.
[5]Abomasal contents of the AH cows contained high levels of *A. fumigatus*. Gut samples distal to the abomasum were negative. Source: OSUCVM (Dr. Jerry Heidel).
[6]Samples were provided by Dr. Mark Rasmussen at the NADC at Iowa State University.
[7]A Dama gazelle was submitted for necropsy at the OSUCVM. It had been fed in the winter in Oregon and was diagnosed with abomasal hemorrhage. Source: OSUSVM (Dr. Rob Bildfell).

TABLE 3

Analysis of clostridial toxin genes with multiplex PCR[1]

| Case/ Location ID | Diagnosis | Blood | Gut contents | Gut wall | Mesenteric lymph node |
|---|---|---|---|---|---|
| WA #1 | JHS | — | | — | |
| Idaho #1 | JHS | | A | | — |
| Idaho #2 | JHS | | — | — | — |
| OSUCVM | AH | | | E | |
| WA#2 | JHS | | — | | |
| Iowa #1 | JHS | — | | — | — |
| Iowa #2 | JHS | a, e | A, E | | — |
| Gazelle OR | AH | | | — | |
| WA #3 | JHS | — | | | |
| 456T | Negative | — | | | |
| 1046 | Negative | — | | | |
| 606N | Negative | — | | | |
| 1099N | Negative | — | | | |

TABLE 3-continued

Analysis of clostridial toxin genes with multiplex PCR[1]

| Case/Location ID | Diagnosis | Blood | Gut contents | Gut wall | Mesenteric lymph node |
|---|---|---|---|---|---|
| S0001 | Negative | — | | | |
| S0002 | Negative | — | | | |
| S0005[2] | Negative | b | | | |
| S0006[2] | Negative | b | | | |
| S0007 | Negative | — | | | |
| S0020[2] | Negative | b | | | |
| S0021 | Negative | — | | | |
| S0023 | Negative | — | | | |
| S0024 | Negative | — | | | |
| S0025 | Negative | — | | | |
| S0026 | Negative | — | | | |
| S0027 | Negative | — | | | |
| S0028 | Negative | — | | | |

[1]Samples were analyzed for clostridial toxin genes by multiplex PCR. Cells lacking any data were not analyzed. "—" indicates non-detectable clostridial toxin genes. "A" and "E" indicate strong α and ε signals, respectively, "a", "b" and "e" indicate weak detection of α, β, and ε toxin genes, respectively. Blank cells were not analyzed.
[2]Cows S0005 and S0006 were from a commercial dairy and had aborted prior to the blood sample. Cow S0020 was a negative control cow in the OSU string.

It will be apparent that the precise details of the methods or compositions described may be varied or modified without departing from the spirit of the described disclosure. We claim all such modifications and variations that fall within the scope and spirit of the claims below.

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred form, the specific embodiments thereof as disclosed and illustrated herein are not to be considered in a limiting sense. Indeed, it should be readily apparent to those skilled in the art in view of the present description that the invention can be modified in numerous ways. The inventor regards the subject matter of the invention to include all combinations and sub-combinations of the various elements, features, functions and/or properties disclosed herein.

What is claimed is:

1. A method of determining an increased risk for jejunal hemorrhage syndrome in a subject, comprising:
    a) obtaining a biological sample from said subject;
    b) amplifying a fungal nucleic acid sequence in the ITS-1 region of *Aspergillus fumigatus* present in said biological sample using at least one primer having at least 90% sequence identity with SEQ ID NO: 11 or SEQ ID NO: 12; and
    c) observing the amplified fungal nucleic acid sequence;
    wherein the presence of said amplified fungal nucleic acid sequence is indicative of an increased risk for jejunal hemorrhage syndrome in said subject.

2. The method of claim 1 wherein observing the amplified fungal nucleic acid sequence comprises measuring the amplified fungal nucleic acid sequence.

3. The method of claim 2, further comprising comparing the amount of said amplified fungal nucleic acid sequence from said biological sample from said subject with the amount of amplified fungal nucleic acid sequence from a biological sample from a negative control subject without jejunal hemorrhage syndrome, wherein the presence of more amplified fungal nucleic acid sequence from said biological sample from said subject compared to the negative control subject is indicative of an increased risk of jejunal hemorrhage syndrome in said subject.

4. The method of claim 1, wherein said primer is SEQ ID NO: 11 or SEQ ID NO: 12.

5. The method of claim 1, wherein said fungal nucleic acid sequence is amplified using a primer consisting of SEQ ID NO: 11 and a primer consisting of SEQ ID NO: 12.

6. The method of claim 1, wherein said subject is of the genus *Bos*.

7. The method of claim 6, wherein said subject is a beef or dairy cow.

8. The method of claim 1, wherein said biological sample is blood.

9. A method of determining an increased risk for jejunal hemorrhage syndrome in a subject, comprising:
    a) amplifying a fungal nucleic acid sequence in the ITS-1 region of *Aspergilius fumigatus* present in a sample of the subject's feed or food using at least one primer having at least 90% sequence identity with SEQ ID NO: 11 or SEQ ID NO: 12; and
    b) observing the amplified nucleic acid sequence;
    wherein the presence of said amplified fungal nucleic acid sequence is indicative of an increased risk of jejunal hemorrhage syndrome in said subject.

10. The method of claim 9 wherein observing the amplified nucleic acid sequence comprises measuring the amplified nucleic acid sequence.

11. The method of claim 9, wherein said primer is SEQ ID NO: 11 or SEQ ID NO: 12.

12. The method of claim 9, wherein said fungal nucleic acid sequence is amplified using a primer consisting of SEQ ID NO: 11 and a primer consisting of SEQ ID NO: 12.

13. The method of claim 9, wherein said subject is of the genus *Bos*.

14. The method of claim 13, wherein said subject is a beef or dairy cow.

* * * * *